US008665452B2

(12) United States Patent
Yan et al.

(10) Patent No.: US 8,665,452 B2
(45) Date of Patent: Mar. 4, 2014

(54) METHOD AND APPARATUS FOR MEASURING THE REFRACTIVE INDEX OF AIR BASED ON THE LASER SYNTHETIC WAVELENGTH INTERFEROMETRY

(75) Inventors: Liping Yan, Zhejiang (CN); Benyong Chen, Zhejiang (CN); Qiuhong Tian, Zhejiang (CN); Zhengrong Sun, Zhejiang (CN)

(73) Assignee: Zhejiang Sci-Tech University, Zhejiang (CN)

( * ) Notice: Subject to any disclaimer, the term of this patent is extended or adjusted under 35 U.S.C. 154(b) by 0 days.

(21) Appl. No.: 13/379,986

(22) PCT Filed: May 18, 2011

(86) PCT No.: PCT/CN2011/074248
§ 371 (c)(1),
(2), (4) Date: Dec. 21, 2011

(87) PCT Pub. No.: WO2012/062096
PCT Pub. Date: May 18, 2012

(65) Prior Publication Data
US 2013/0258348 A1    Oct. 3, 2013

(30) Foreign Application Priority Data
Nov. 12, 2010 (CN) .......................... 2010 1 0545458

(51) Int. Cl.
*G01N 21/41* (2006.01)
*G01N 21/43* (2006.01)
(52) U.S. Cl.
USPC .......................................... 356/517; 356/484
(58) Field of Classification Search
USPC ......... 356/128, 517–521, 481, 498, 500, 486, 356/484
See application file for complete search history.

(56) References Cited

U.S. PATENT DOCUMENTS

| | | | | |
|---|---|---|---|---|
| 4,733,967 A | * | 3/1988 | Sommargren | 356/484 |
| 5,231,285 A | * | 7/1993 | Berg | 250/231.1 |
| 5,394,244 A | * | 2/1995 | Tsai | 356/517 |
| 6,252,668 B1 | * | 6/2001 | Hill | 356/487 |
| 6,330,065 B1 | * | 12/2001 | Hill | 356/485 |

(Continued)

FOREIGN PATENT DOCUMENTS

| CN | 1103161 | 5/1995 |
|---|---|---|
| CN | 1095542 | 7/2000 |

(Continued)

*Primary Examiner* — Tarifur Chowdhury
*Assistant Examiner* — Michael P LaPage
(74) *Attorney, Agent, or Firm* — Workman Nydegger

(57) ABSTRACT

Measuring refractive index of air based on laser synthetic wavelength interferometry. The Apparatus includes a dual-frequency laser that emits orthogonal linear polarized light of wavelengths $\lambda_1$ and $\lambda_2$, a beamsplitter, two polarizing beam-splitters, two corner-cube retroreflectors, a quartz vacuum cavity of length L disposed in the measuring optical path in parallel to the light propagation direction, and two detectors. The apparatus is used to measure the refractive index of air using the dual-frequency laser to emit orthogonal linear polarized light with wavelengths $\lambda_1$ and $\lambda_2$, using the beam-splitters, corner-cube retroreflectors, quartz vacuum cavity, and detectors. The integer N and fraction $\epsilon$ of interference fringes of wavelength $\lambda_2$ are determined. The refractive index of air n is obtained by using the length L of the vacuum cavity, integer N and fraction $\epsilon$ of the interference fringes of wavelength $\lambda_2$. The measurement is accurate up to $10^{-9}$ or higher, and has strong anti-disturbance ability to the environment.

3 Claims, 1 Drawing Sheet

(56) References Cited

U.S. PATENT DOCUMENTS

| | | | |
|---|---|---|---|
| 6,417,927 B2 * | 7/2002 | de Groot | 356/517 |
| 6,559,951 B2 * | 5/2003 | Ishikawa et al. | 356/517 |
| 2001/0043334 A1 * | 11/2001 | Ishikawa et al. | 356/517 |
| 2002/0140946 A1 * | 10/2002 | Groot et al. | 356/517 |
| 2012/0081698 A1 * | 4/2012 | Christian et al. | 356/128 |

FOREIGN PATENT DOCUMENTS

| | | |
|---|---|---|
| CN | 102033053 | 4/2011 |
| DE | 4403021 | 8/1994 |
| DE | 10115292 | 10/2001 |
| DE | 102005027023 | 12/2006 |
| WO | WO9942875 | 8/1999 |

* cited by examiner

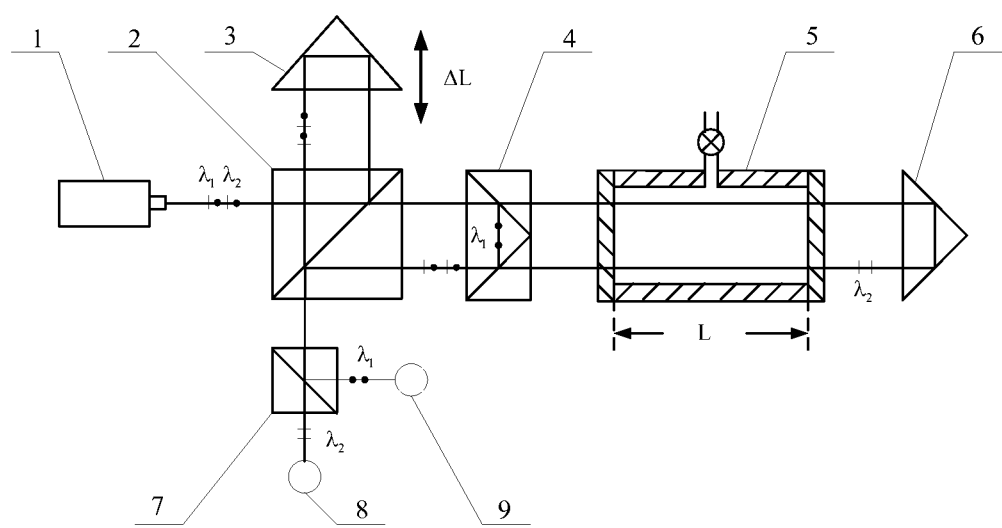

METHOD AND APPARATUS FOR MEASURING THE REFRACTIVE INDEX OF AIR BASED ON THE LASER SYNTHETIC WAVELENGTH INTERFEROMETRY

TECHNICAL FIELD

The present invention relates to a method and an apparatus for measuring the refractive index of air, and specifically to a method and an apparatus for measuring the refractive index of air based on the laser synthetic wavelength interferometry.

BACKGROUND OF THE INVENTION

Since the length unit "meter" was defined as that "the meter is the length of the path travelled by light in vacuum during a time interval of $1/299\ 792\ 458$ of a second" in the 17th General Conference of Weights & Measures in October 1983, the CIPM has recommended, in succession, twelve light radiation wavelengths as optical wavelength standards. Later, various optical measurement methods using a laser wavelength as a length "ruler" were widely applied in research areas such as metrology, information science, communication, astronomy and so on. As various optical measurement methods are often performed in the air and the value of laser wavelength in the air is closely related to the refractive index of air, the measurement accuracy of the refractive index of air becomes one factor so important that restricts the improvement of accuracy for various optical measurement methods which take the laser wavelength as the length standard.

Methods for measuring the refractive index of air are generally classified into two types, i.e. the type of indirect measurement and the type of direct measurement. The indirect measurement method calculates the refractive index of air with the Edlén equation after measuring the pressure, the temperature and the relative humidity of the air. As the Edlén equation is obtained under a standard condition of the air, the difference between the composition of the air in the measurement environment and that of the standard air may cause an error in the measurement result. Even though the refractive index of air could be further rectified by measuring the content of carbon dioxide in the air, the measurement accuracy of the method cannot be better than $3\times10^{-8}$ due to the measurement uncertainties from various air parameter sensors. Therefore, in some circumstances requiring precision measurement of a large-range with high-accuracy (for example, the ratio of measurement accuracy to measurement range is less than $10^{-9}$), it is necessary to measure the refractive index of air directly.

The direct measurement for the refractive index of air is usually achieved by use of interferometry including the multiple-wavelength laser interferometry, the Rayleigh interferometry, the evacuation measurement, the Fabry-Perot interferometry, the dual-wavelength interferometry and so on. Interferometry for measuring the refractive index of air generally takes the refractive index of the vacuum for reference to measure the number of interference fringes produced by the optical path difference when the light travels over two optical paths with the same length L both in the vacuum and in the air, i.e. $2L\cdot(n-1)=(N+\epsilon)\cdot\lambda_0$ (wherein n is the refractive index of air, N is the integer of the interference fringes, and $\epsilon$ is the fraction of the interference fringes). When using interferometry for measuring the refractive index of air, the measurement accuracy depends on the subdivision coefficient of the interference fringes, and the length L of the optical path both in the vacuum and in the air. For example, when the L is 100 mm, and $\lambda_0=633$ nm, if it is desired to obtain a resolution of $10^{-9}$ for the refractive index of air n, it is necessary for the subdivision coefficient of the interference fringes to be $K=1/3150$. This may complicate the structure of the measurement system with a high cost. Therefore, in the prior art, most of the measurement accuracies for the refractive index of air on the basis of interferometry can but reach up to $10^{-8}$.

SUMMARY OF THE INVENTION

In order to satisfy the need for a high accuracy of refractive index of air in such technical fields as precision measurement, laser interferometer, laser radar and etc., it is an object of the present invention to provide a method and an apparatus for measuring the refractive index of air based on the laser synthetic wavelength interferometry, which method and apparatus are capable of carrying out a precision measurement for the fraction of the interference fringes corresponding to a variation of the refractive index of air based on the principle of subdivision of laser synthetic wavelength interference fringes.

The technical solutions adopted by the present invention for solving its technical problem are:

I. A method for measuring the refractive index of air based on the laser synthetic wavelength interferometry:

using a dual-frequency laser to output orthogonal linear polarization lights with wavelengths $\lambda_2$ and $\lambda_2$; emitting the orthogonal linear polarization lights to a laser synthetic wavelength interferometer comprising a beamsplitter, a first polarizing beamsplitter, a second polarizing beamsplitter, a first corner-cube retroreflector and a second corner-cube retroreflector; in the measuring optical path of the interferometer, a quartz vacuum cavity of a length L being disposed in parallel to the light propagation direction; receiving interference signals of the wavelengths $\lambda_1$ and $\lambda_2$ respectively by a first detector and a second detector when moving the first corner-cube retroreflector of the interferometer; before starting to measure the refractive index of air, evacuating the quartz vacuum cavity; moving the first corner-cube retroreflector of the interferometer to find a position where the phase difference between the two interference signals of the wavelengths $\lambda_1$ and $\lambda_2$ is set to an original value of zero; then introducing air into the quartz vacuum cavity until the air inside the cavity is consistent with air outside, during this process, taking the interference signal of the wavelength $\lambda_1$ as a reference signal; firstly, using the first detector of photoelectric type to directly detect the integer N of the interference fringes of the wavelength $\lambda_2$, and then moving the first corner-cube retroreflector of the interferometer such that the phase difference between the interference signals of the wavelengths $\lambda_1$ and $\lambda_2$ becomes zero again; according to the principle of subdivision of laser synthetic wavelength interference fringes, measuring and obtaining the fraction $\epsilon$ of the interference fringes of the wavelength $\lambda_2$ resulted from change of the refractive index of air; and finally, calculating the refractive index of air according to relation of the refractive index of air n to the length L of the vacuum cavity, the number N and $\epsilon$ of the interference fringes as follows:

$$n-1 = \frac{(N+\varepsilon)\cdot\lambda_{20}}{2L} \quad (1)$$

Wherein, $\lambda_{22}$ is the vacuum wavelength.

II. An apparatus for measuring the refractive index of air based on the laser synthetic wavelength interferometry:

The apparatus of the present invention comprises: a dual-frequency laser, a beamsplitter, a first corner-cube retroreflector, a second corner-cube retroreflector, a first polarizing beamsplitter, a second polarizing beamsplitter, a quartz vacuum cavity, a first detector and a second detector, wherein orthogonal linear polarization lights with wavelengths $\lambda_1$ and $\lambda_2$ outputted by the dual-frequency laser are emitted to a laser synthetic wavelength interferometer consisting of the beamsplitter, the first corner-cube retroreflector, the first polarizing beamsplitter, the second corner-cube retroreflector and the second polarizing beamsplitter, so as to form respective interference signals; these interference signals are received by the first detector and the second detector, respectively, after they are split by the second polarizing beamsplitter; the quartz vacuum cavity is disposed between the first polarizing beamsplitter and the second corner-cube retroreflector in the measuring optical path of the interferometer.

The beneficial effects of the present invention are:

1. According to the present invention, the measurement of the fraction ε of the interference fringes due to variation of the refractive index of air is converted to the measurement of the displacement of the corner-cube retroreflector (in a millimeter or micron range) which is easier for detection, instead of using the method of direct subdivision of the interference fringes to measure the fraction of the interference fringes, thus capable of achieving the measurement of the refractive index of air with high accuracy. Moreover, the method of the present invention is simple in optical path configuration and convenient for use.

2. The measurement of the refractive index of air according to the present invention can achieve an accuracy up to $10^{-9}$ or higher, with advantages of high measurement accuracy and strong anti-disturbance ability to the environment, and can be applied to such technical fields as precise measurement, laser interferometer, laser radar and so on.

BRIEF DESCRIPTION OF THE DRAWINGS

FIG. 1 is the schematic diagram of an apparatus for measuring the refractive index of air based on the laser synthetic wavelength interferometry.

In the drawing: 1. dual-frequency laser; 2. beamsplitter; 3. first corner-cube retroreflector; 4. first polarizing beamsplitter; 5. quartz vacuum cavity; 6. second corner-cube retroreflector; 7. second polarizing beamsplitter; 8. first detector; 9. second detector.

DETAILED DESCRIPTION OF THE PREFERRED EMBODIMENTS

As shown in FIG. 1, the apparatus for measuring the refractive index of air based on the laser synthetic wavelength interferometry according to the present invention comprises: a dual-frequency laser 1, a beamsplitter 2, a first corner-cube retroreflector 3, a first polarizing beamsplitter 4, a quartz vacuum cavity 5, a second corner-cube retroreflector 6, a second polarizing beamsplitter 7, a first detector 8 and a second detector 9. The orthogonal linear polarization lights with wavelengths $\lambda_1$ and $\lambda_2$ outputted by the dual-frequency laser 1 are emitted to a laser synthetic wavelength interferometer which comprises the beamsplitter 2, the first corner-cube retroreflector 3, the first polarizing beamsplitter 4, the second corner-cube retroreflector 6 and the second polarizing beamsplitter 7, so as to form respective interference signals. These interference signals, after being split by the second polarizing beamsplitter 7, are received by the first detector 8 and the second detector 9, respectively. The quartz vacuum cavity 5 is disposed between the first polarizing beamsplitter 4 and the second corner-cube retroreflector 6 in the measuring optical path of the interferometer.

According to the principle of subdivision of laser synthetic wavelength interference fringes, in the apparatus shown in the drawing, a subdivision coefficient of the interference fringes is obtained as follows:

$$K = \frac{\lambda_2}{\lambda_S} \qquad (2)$$

wherein the $\lambda_S$ is a synthetic wavelength formed by $\lambda_1$ and $\lambda_2$, and $\lambda_S = \lambda_1\lambda_2/=\lambda_1-\lambda_2=$.

When the wavelengths $\lambda_1$ and $\lambda_2$ outputted by the dual-frequency laser 1 have a frequency difference of 1 GHz, the subdivision coefficient of the interference fringes for the wavelength $\lambda_2$ can be obtained as: K=1/440000. Therefore, by means of this method for subdividing the interference fringes, the fraction ε of the interference fringes of $\lambda_2$ in Equation (1) corresponding to the variation of the refractive index of air can be precisely measured with high accuracy and high resolution.

The detailed measurement of the refractive index of air is performed as follows:

Before the measurement, the quartz vacuum cavity 5 is evacuated. The first corner-cube retroreflector 3 is moved to make the phase difference between the interference signals of the wavelengths $\lambda_1$ and $\lambda_2$ to be zero (i.e. Δφ=0). Then the air is slowly introduced into the quartz vacuum cavity 5 until the air inside the cavity is consistent with the air outside. During this process, the refractive index of air inside the cavity varies gradually from 1 to the outside refractive index of air n. The variation of the refractive index of air inside the cavity will cause an increased optical path of the wavelength $\lambda_2$, allowing the signal of interference fringes of the wavelength $\lambda_2$ to vary. During this process, the interference signal of the wavelength $\lambda_1$ received by the second detector 9 is used as a reference signal, and the interference signal of the wavelength $\lambda_2$ received by the first detector 8 is used as a measuring signal. Firstly, the first detector 8 of photoelectric type is used to directly detect an integer N of the interference fringes of the wavelength $\lambda_2$, and then the first corner-cube retroreflector 3 is moved such that the phase difference between the interference signals of the wavelengths $\lambda_1$ and $\lambda_2$ becomes zero again. According to the principle of subdivision of laser synthetic wavelength interference fringes, the fraction ε of the interference fringes of the wavelength $\lambda_2$ resulted from the variation of the refractive index of air is measured as:

$$\varepsilon \cdot \frac{\lambda_{20}}{2} = \frac{\lambda_2}{\lambda_S} \cdot \Delta L \qquad (3)$$

Wherein: ΔL is the displacement of the first corner-cube retroreflector 3 (in a millimeter or micron range).

By substituting the measured integer N and fraction ε of the interference fringes of $\lambda_2$ into Equation (1), the refractive index of air n can be calculated:

$$n - 1 = N \cdot \frac{\lambda_{20}}{2L} + \frac{\lambda_2}{\lambda_S} \cdot \frac{\Delta L}{L} \qquad (4)$$

Substituting the typical values (wherein the wavelengths $\lambda_1$ and $\lambda_2$ have a frequency difference of 1 GHz) to calculate: when the first corner-cube retroreflector 3 has a movement accuracy of 0.1 μm and the quartz vacuum cavity 5 has a length L of 100 mm, the measurement accuracy of the refractive index of air can be up to $2.3 \times 10^{-12}$.

What is claimed is:

1. A method for measuring the refractive index of air based on laser synthetic wavelength interferometry, the method comprising:

using a dual-frequency laser to output orthogonal linear polarization lights with wavelengths $\lambda_1$ and $\lambda_2$;

emitting the orthogonal linear polarization lights to a laser synthetic wavelength interferometer composed of a beamsplitter, a first polarizing beamsplitter, a second polarizing beamsplitter, a first corner-cube retroreflector, and a second corner-cube retroreflector;

providing, in a measuring optical path of the interferometer, a quartz vacuum cavity of a length L and being disposed in parallel to a light propagation direction;

providing a first detector and a second detector of photoelectric type for receiving interference signals of the wavelengths $\lambda_1$ and $\lambda_2$, respectively, when moving the first corner-cube retroreflector of the interferometer;

before starting to measure the refractive index of air, evacuating the quartz vacuum cavity, receiving interference signals of the wavelengths $\lambda_1$ and $\lambda_2$, and moving the first corner-cube retroreflector to find a position where the phase difference between the interference signals of the wavelengths $\lambda_1$ and $\lambda_2$ is set to an original value of zero;

then introducing air into the quartz vacuum cavity until the air inside the cavity is consistent with air outside and taking the interference signal of the wavelength $\lambda_1$ as a reference signal;

using the first detector to directly detect an integer N of interference fringes of the wavelength $\lambda_2$;

then receiving interference signals of the wavelengths $\lambda_1$ and $\lambda_2$ and moving the first corner-cube retroreflector such that the phase difference between the interference signals of the wavelengths $\lambda_1$ and $\lambda_2$ becomes zero again;

according to principle of subdivision of laser synthetic wavelength interference fringes, measuring and obtaining a fraction $\epsilon$ of the interference fringes of the wavelength $\lambda_2$ resulting from variation of the refractive index of air as follows $$\varepsilon \cdot \frac{\lambda_{20}}{2} = \frac{\lambda_2}{\lambda_S} \cdot \Delta L$$

wherein
ΔL is the displacement of the first corner-cube retroreflector,
$\lambda_{20}$ is the vacuum wavelength, and
$\lambda_s$ is a synthetic wavelength formed by $\lambda_1$ and $\lambda_2$; and finally, calculating the refractive index n of air according to the relation of the refractive index of air n to the length L of the vacuum cavity, and the number N and fraction ε of the interference fringes as follows:

$$n - 1 = \frac{(N + \varepsilon) \cdot \lambda_{20}}{2L}.$$

2. A method for measuring the refractive index of air based on laser synthetic wavelength interferometry, the method comprising:

using a dual-frequency laser to output orthogonal linear polarization lights with wavelengths $\lambda_1$ and $\lambda_2$;

emitting the orthogonal linear polarization lights to a laser synthetic wavelength interferometer composed of a beamsplitter, a first polarizing beamsplitter, a second polarizing beamsplitter, a first corner-cube retroreflector, and a second corner-cube retroreflector;

providing, in a measuring optical path of the interferometer, a quartz vacuum cavity of a length L and being disposed in parallel to a light propagation direction;

providing a first detector and a second detector of photoelectric type for receiving interference signals of the wavelengths $\lambda_1$ and $\lambda_2$, respectively, when moving the first corner-cube retroreflector of the interferometer;

before starting to measure the refractive index of air, evacuating the quartz vacuum cavity, receiving interference signals of the wavelengths $\lambda_1$ and $\lambda_2$, and moving the first corner-cube retroreflector to find a position where the phase difference between the interference signals of the wavelengths $\lambda_1$ and $\lambda_2$ is set to an original value of zero;

then introducing air into the quartz vacuum cavity until the air inside the cavity is consistent with air outside and taking the interference signal of the wavelength $\lambda_1$ as a reference signal;

using the first detector to directly detect an integer N of interference fringes of the wavelength $\lambda_2$;

then receiving interference signals of the wavelengths $\lambda_1$ and $\lambda_2$ and moving the first corner-cube retroreflector such that the phase difference between the interference signals of the wavelengths $\lambda_1$ and $\lambda_2$ becomes zero again;

according to principle of subdivision of laser synthetic wavelength interference fringes, measuring and obtaining a fraction of the interference fringes of the wavelength $\lambda_2$ resulting from variation of the refractive index of air; and finally, calculating the refractive index n of air as follows:

$$n - 1 = N \cdot \frac{\lambda_{20}}{2L} + \frac{\lambda_2}{\lambda_S} \cdot \frac{\Delta L}{L}$$

wherein
$\lambda_{20}$ is the vacuum wavelength,
L is the length of the quartz vacuum cavity,
$\lambda_s$ is a synthetic wavelength formed by $\lambda_1$ and $\lambda_2$, and
ΔL is the displacement of the first corner-cube retroreflector.

3. An apparatus for measuring the refractive index of air based on laser synthetic wavelength interferometry, the apparatus comprising:

a dual-frequency laser that is configured to emit orthogonal linear polarization lights with wavelengths $\lambda_1$ and $\lambda_2$;

a laser synthetic wavelength interferometer composed of:
a beamsplitter;
a first corner-cube retroreflector;
a first polarizing beamsplitter;
a second corner-cube retroreflector; and a second polarizing beamsplitter, the laser synthetic wavelength interferometer being positioned so as to receive the orthogonal linear polarization lights with wavelengths $\lambda_1$ and $\lambda_2$ emitted by the dual-frequency laser and form respective interference signals for each of the wavelengths $\lambda_1$ and $\lambda_2$;

a quartz vacuum cavity of length L disposed between the first polarizing beamsplitter and the second corner-cube retroreflector in a measuring optical path of the interferometer;

first and second detectors of photoelectric type, the first and second detectors being configured to receive interference signals for each of the wavelengths $\lambda_1$ and $\lambda_2$, respectively, when moving the first corner-cube retroreflector of the interferometer in two operations: (1) when the quartz vacuum cavity has been evacuated and the first corner-cube retroreflector is moved a first time to find a position where the phase difference between the interference signals of the wavelengths $\lambda_1$ and $\lambda_2$ is set to an original value of zero and (2) when the quartz vacuum cavity is filled with air and the first corner-cube retroreflector is moved a second time such that the phase difference between the interference signals of the wavelengths $\lambda_1$ and $\lambda_2$ becomes zero again, the first detector being configured to directly detect an integer N of interference fringes of the wavelength $\lambda_2$ after (1) and before (2); and a computer programmed to calculate the refractive index n of air from the following algorithm:

$$n - 1 = N \cdot \frac{\lambda_{20}}{2L} + \frac{\lambda_2}{\lambda_S} \cdot \frac{\Delta L}{L}$$

wherein $\lambda_{20}$ is the vacuum wavelength,

L is the length of the quartz vacuum cavity, $\lambda_S$ is a synthetic wavelength formed by $\lambda_1$ and $\lambda_2$, and $\Delta L$ is the displacement of the first corner-cube retroreflector.

* * * * *